United States Patent

Tokizawa et al.

[11] Patent Number: 5,986,144
[45] Date of Patent: Nov. 16, 1999

[54] TRIAZOLE DERIVATIVE, PREPARATION PROCESS THEREOF AND PHARMACEUTICAL COMPRISING THE SAME AS AN EFFECTIVE INGREDIENT

[75] Inventors: Minoru Tokizawa, Narita; Sunao Takeda, Ichihara; Yasushi Kaneko, Narita; Hiromichi Eto, Narita; Kazuya Ishida, Narita; Kazunori Maebashi, Narashino; Masaru Matsumoto, Tomisato-machi; Takemitsu Asaoka; Susumu Sato, both of Narita; Hideaki Matsuda, Abiko, all of Japan

[73] Assignee: SS Pharmaceutical Co., Ltd., Tokyo, Japan

[21] Appl. No.: 09/311,057

[22] Filed: May 14, 1999

Related U.S. Application Data

[62] Division of application No. 08/767,694, Dec. 17, 1996.

[30] Foreign Application Priority Data

Dec. 22, 1995 [JP] Japan .................................. 7-335251

[51] Int. Cl.[6] .................................................. C07C 323/07
[52] U.S. Cl. .................................................. 568/43
[58] Field of Search .................................................. 568/43

[56] References Cited

U.S. PATENT DOCUMENTS

| 4,616,026 | 10/1986 | Richardson et al. ................. 514/381 |
| 4,661,507 | 4/1987 | Gymer et al. ................. 514/383 |
| 5,004,494 | 4/1991 | Sugavanam et al. ................. 71/92 |
| 5,147,886 | 9/1992 | Tokizawa et al. ................. 514/383 |
| 5,605,921 | 2/1997 | Imaizumi et al. ................. 514/383 |

FOREIGN PATENT DOCUMENTS

| 0 113 640 | 7/1984 | European Pat. Off. . |
| 0 117 100 | 8/1984 | European Pat. Off. . |
| 0 415 320 | 3/1991 | European Pat. Off. . |
| 0 435 081 | 7/1991 | European Pat. Off. . |

OTHER PUBLICATIONS

Burger, "Medicinal Chemistry", 2$^{nd}$ Ed. NY, 1055.
Chemical Abstracts, vol. 116, No. 25, Jun. 22, 1992, JP 03 284 662, Dec. 16, 1991.
Donald J. Cram, "Organic Chemistry", McGraw–Hill Book Co., NY, (1964), 2$^{nd}$ Edition, pp. 565–567.

*Primary Examiner*—Patricia L. Morris
*Attorney, Agent, or Firm*—Oblon, Spivak, McClelland, Maier & Neustadt, P.C.

[57] ABSTRACT

Described is a triazole derivative represented by the formula (1) or salt thereof, preparation process thereof, preparation intermediates represented by the formulas (2) and (3), and a pharmaceutical comprising the compound represented by the formula (1) or salt thereof.

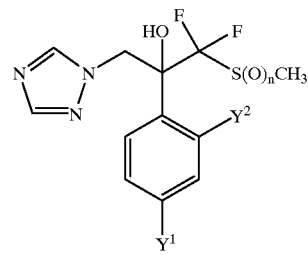

(1)

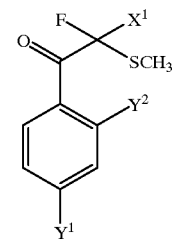

(2)

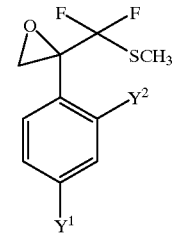

(3)

wherein n stands for 0, 1 or 2, $X^1$ represents H or F and $Y^1$ and $Y^2$ each independently represents H, halogen or $CF_3$.

1 Claim, No Drawings

TRIAZOLE DERIVATIVE, PREPARATION PROCESS THEREOF AND PHARMACEUTICAL COMPRISING THE SAME AS AN EFFECTIVE INGREDIENT

This is a Division of application Ser. No. 08/767,694, filed Dec. 17, 1996, now allowed.

BACKGROUND OF THE INVENTION

1. Field of the Invention

This invention relates to a novel triazole derivative, and more specifically to a novel triazole derivative having both excellent antimycotic action and high safety, a pharmaceutical comprising the derivative as an effective ingredient, an intermediate of the derivative and preparation process of the derivative.

2. Description of the Related Art

Mycosis can be classified into two types, that is, superficial mycosis represented by various trichophytosis, marginated eczema, psoriasis, cutaneous candidiasis or the like and deep seated mycosis represented by mycotic meningitis, mycotic infectious disease of respiratory organ, fungemia, mycosis of urinary tract or the like. Of these, deep seated mycosis such as candidiasis or aspergillosis tends to show a marked increase in recent days owing to the frequent use of an anticancer chemotherapeutic agent or immunosuppressive agent or lowering in the bioimmunology due to HIV infection or the like. There is accordingly a demand for a pharmaceutical efficacious against such fungi.

As a pharmaceutical effective against Aspergillus and Candida, Amphotericin B and azole-based compounds such as Fluconazole and Itraconazole are conventionally known, but the number of such pharmaceuticals is not so many yet. So, more effective mycocides are under research and development. For example, a methanesulfonyl-containing compound (Japanese Patent Application Laid-Open No. 85369/1986, Japanese Patent Application Laid-Open No. 223266/1991 or the like) and a difluoromethylene-containing compound (Japanese Patent Application Laid-Open No. 163374/1984, Japanese Patent Application Laid-Open No. 163269/1993 or the like) are known as an azole-based compound.

Therapeutics for deep seated mycosis which have so far been known each has problems in safety and antimycotic action and is not always effective against Aspergillus or Candida. Accordingly, an object of the present invention is to provide a compound which has strong antimycotic action, is effective against Aspergillus and Candida and has high safety; and a pharmaceutical comprising the compound as an effective ingredient.

With the forgoing in view, the present inventors synthesized a number of triazole derivatives and carried out an investigation on the antimycotic action of these derivatives. As a result, it has been found that a triazole derivative represented by the below-described formula (1) and a salt thereof have excellent antimycotic action against Aspergillus and Candida and at the same time have high safety so that it is useful as a pharmaceutical, leading to the completion of the present invention.

SUMMARY OF THE INVENTION

The present invention therefore provides a triazole derivative represented by the following formula (1):

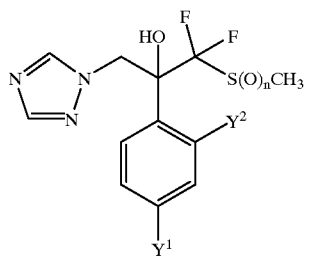

(1)

wherein $Y^1$ and $Y^2$ are the same or different and each independently represents a hydrogen atom, a halogen atom or a trifluoromethyl group and n stands for 0, 1 or 2, or salt thereof; a pharmaceutical comprising the compound as an effective ingredient, an intermediate of the compound and a preparation process of the compound.

The present invention also provides the use of the triazole derivative represented by the above formula (1) or salt thereof as a pharmaceutical.

The present invention further provides a treating method of mycosis, which comprises administering to a patient an effective amount of the triazole derivative represented by the above formula (1) or salt thereof.

The triazole derivative (1) according to the present invention has strong antimycotic action, is effective against Aspergillus and Candida; and at the same time has high safety so that it is considerably useful as a pharmaceutical such as a mycocide.

DETAILED DESCRIPTION OF THE PREFERRED EMBODIMENTS

Examples of the halogen atom in the above formula (1) include fluorine, chlorine, bromine and iodine atoms. Of these, fluorine and chlorine atoms are preferred.

No particular limitation is imposed on the salt of the triazole derivative (1) of the present invention insofar as it is a pharmacologically acceptable salt. Examples include acid addition salts such as hydrochloride, nitrate, hydrobromide, p-toluenesulfonate, methanesulfonate, fumarate, succinate and lactate.

The triazole derivative (1) or salt thereof according to the present invention has stereoisomers based on an asymmetric carbon or sulfoxide. The present invention embraces these stereoisomers and also isomer mixtures such as racemic modification. The triazole derivative (1) or salt thereof sometimes exists in the form of a solvate represented by a hydrate. The present invention also embraces such solvates.

The triazole derivative (1) of the present invention can be prepared, for example, in accordance with the following reaction scheme:

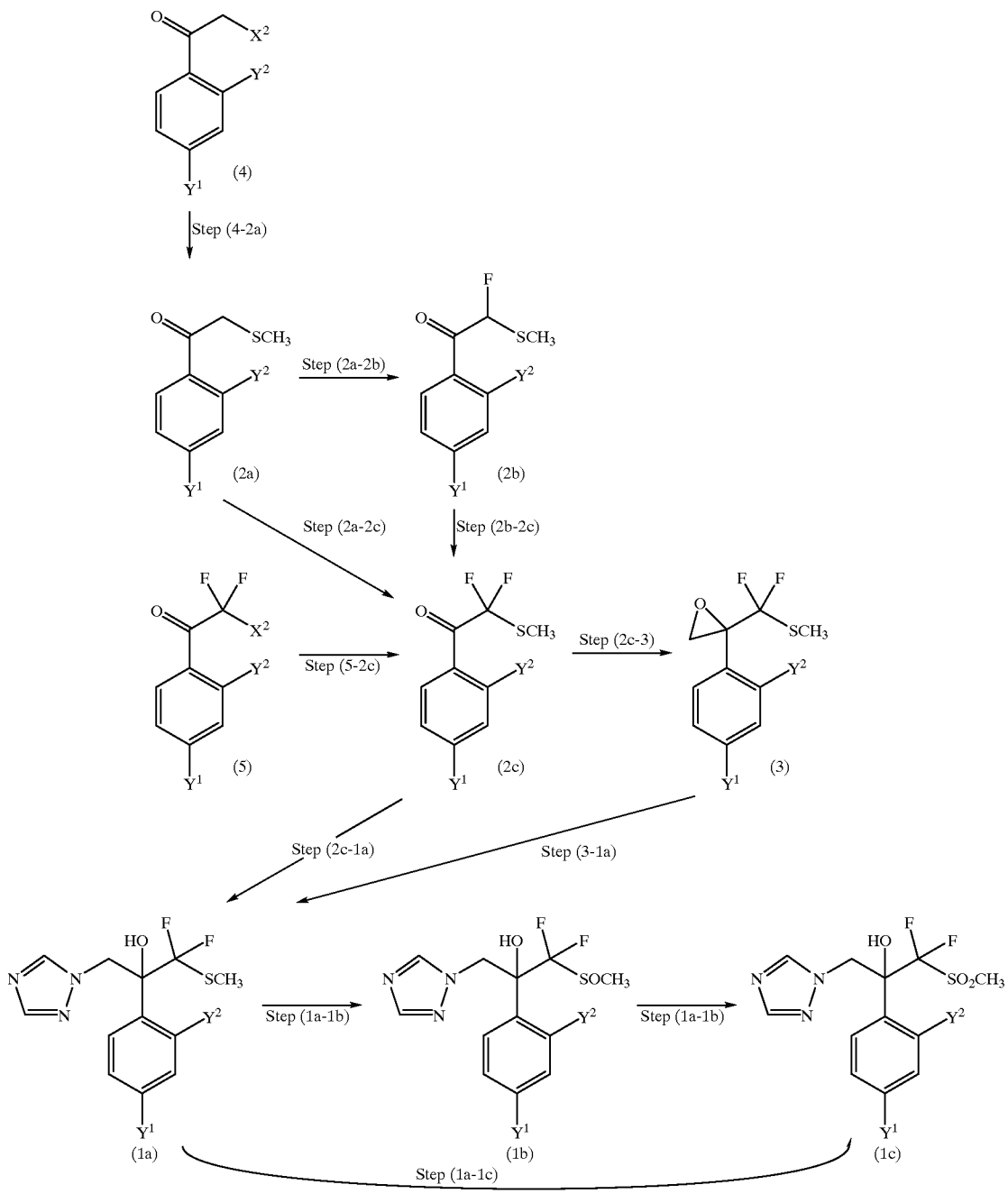

wherein $X^1$ represents a halogen atom and $Y^1$ and $Y^2$ have the same meanings as defined above.

Described specifically, Compound (1a) wherein in the formula (1), n stands for 0 can be prepared by introducing a methylthio group into a 2-halo-acetophenone derivative (4), which is a known compound, thereby converting the derivative into Compound (2a); preparing a 2,2-difluoro-2-(methylthio)acetophenone derivative (2c) directly from Compound (2a) or through a 2-fluoro-2-(methylthio) acetophenone derivative (2b), or by introducing a methylthio group into a 2,2-difluoro-2-substituted acetophenone derivative (5) which is a known compound; and triazolemethylating the resulting Compound (2c) or subsequent to the epoxymethylation of the resulting Compound (2c) into Compound (3), introducing a triazole group into Compound (3). By oxidizing Compound (1a) so obtained, Compound (1b) wherein in the formula (1), n stands for 1 and Compound (1c) wherein in the formula (1) n stands for 2 can be prepared. Here, Compound (1c) can also be prepared by oxidizing Compound (1b). Incidentally, not only Compounds (1a), (1b) and (1c) but also the above-described intermediates (2b), (2c) and (3) are novel compounds which have not been reported in publications and are embraced by the present invention.

The present invention will hereinafter be described in accordance with the above steps.

Step (4-2a)

Compound (2a) can be prepared by introducing a methylthio group into Compound (4).

Concerning Compound (4) which is a raw material, examples of $X^2$ in the formula (4) include fluorine, chlorine and bromine atoms, with a chlorine atom being preferred. Examples of the halogen atom represented by $Y^1$ or $Y^2$ include fluorine, chlorine and bromine atoms, with a fluorine atom being preferred. Of Compounds (4), a compound wherein $X^2$ represents a fluorine, chorine or bromine atom and $Y^1$ and $Y^2$ represent fluorine atoms at the same time is commercially available, for example, from Aldrich Chemical Co., Inc.

Examples of the methylthio-introducing reagent include a metal salt, such as sodium salt or potassium salt, of methylmercaptan, and aqueous solutions and methanol solutions thereof. Of these, an aqueous solution of a sodium salt of methylmercaptan is preferred. Examples of the reaction solvent include alcohol-based solvents such as methanol or ethanol, N,N-dimethylformamide, 1,4-dioxane and tetrahydrofuran. Of these, alcohol-based solvents, particularly methanol, is preferred.

Step (2a-2c)

Compound (2c) can be prepared by reacting Compound (2a) with a fluorinating reagent in a solvent.

Examples of the fluorinating reagent include fluorine gas, perchloryl fluoride, potassium fluoride, spray-dried potassium fluoride, freeze-dried potassium fluoride, tetraalkylammonium fluoride, tris(dimethylamino)sulfa(trimethylsilyl)difluoride, N-fluoropyridone, N-fluoro-N-alkyl-arenesulfonamide, N-fluoroquinuclidinium salt, N-fluoroperfluoroalkyl sulfonimide, N-fluorosaltum, fluorinated xenone, N-fluoropyridinium salt and N-fluoropyridinium sulfonate. Examples of the commercially available fluorinating agent include "Onoda Fluorinates FP-T300, FP-T500, FP-T700, FP-B300, FP-B500, FP-B700 and FP-B800" (trade names; products of Chichibu Onoda Co., Ltd.) and "MEC-01, MEC-02, MEC-03, MEC-04, MEC-05" (trade names; Products of Daikin Industries, Ltd.). It is preferred to use the fluorinating reagent in an amount of 2–20 equivalents per mole of Compound (2a). Illustrative of the usable reaction solvent include 1,2-dichloroethane, 1,1,2-trichloroethane, chloroform, methylene chloride, diethyl ether, ethyl acetate and tetrahydrofuran. Of these, 1,1,2-trichloroethane is particularly preferred. The reaction temperature preferably falls within a range of from −78° C. to the boiling point of a solvent, with 80–100° C. being particularly preferred.

To improve the yield of the compound, a Lewis acid or a base can be used. Exemplary Lewis acid include aluminum chloride, zinc chloride and tin chloride, while exemplary base include sodium hydroxide, potassium hydroxide, barium hydroxide, sodium carbonate, potassium carbonate, sodium hydride, potassium tert-butoxide, lithium diisopropylamide and potassium hexamethyldisilazane.

Step (2a-2b) and Step (2b-2c)

Compound (2c) can also be prepared through Compound (2b). In this case, Compound (2b) and Compound (2c) can be synthesized by reacting Compound (2a) and Compound (2b), respectively, with a fluorinating reagent in a solvent, similar to the case where Compound (2c) is synthesized directly from Compound (2a). Upon synthesis, the fluorinating reagent, solvent, Lewis acid and base similar to those employed in the previous step (2a-2c) can be used. In the synthesizing reaction of Compound (2b) from Compound (2a), the fluorinating reagent is used preferably in an amount of 1–2 equivalents per mole of Compound (2a), with an amount of 1–1.5 equivalents being particularly preferred. As the solvent, 1,2-dichloroethane is particularly preferred and as the reaction temperature, 20–40° C. is particularly preferred. In the synthesizing reaction of Compound (2c) from Compound (2b), it is preferred to use the fluorinating reagent in an amount of 1–2 equivalents per mole of Compound (2b), with 1–1.5 equivalents being particularly preferred. As the solvent and the reaction temperature, 1,1,2-trichloroethane and 80–100° C. are particularly preferred, respectively.

Step (5-2c)

Compound (2c) can also be prepared by introducing a methylthio group into Compound (5). In this case, as the methylthio-introducing reagent, sodium methylmercaptan and an aqueous solution thereof can be given as examples. It is preferred to use the methylthio-introducing reagent in an amount of 1–2 equivalents relative to Compound (5). Examples of the reaction solvent include methanol, N,N-dimethylformamide and dimethylsulfoxide. The reaction temperature preferably falls within a range of from −78° C. to the boiling point of the solvent, with a range of from −20° C. to 50° C. being particularly preferred.

Step (2c-1a)

The direct synthesis of Compound (1a) from Compound (2c) is effected by reacting one mole of Compound (2c) with 1–2 moles of an epoxymethylating agent and 1–4 moles of 1,2,4-triazole or alkali metal salt thereof in a solvent in the presence of 2–5 moles of a base at −100° C. to room temperature or under reflux for 1–30 hours. Examples of the epoxymethylating agent include trimethylsulfoxonium iodide and trimethylsulfonium iodide. Illustrative of the base include sodium hydroxide, potassium hydroxide, barium hydroxide, sodium carbonate, potassium carbonate and sodium hydride. Of these, potassium hydroxide is particularly preferred. Exemplary reaction solvent include alcohols such as methanol, ethanol, isopropanol, n-butanol, sec-butanol or tert-butanol.

Step (2c-3)

Compound (1a) can also be prepared from Compound (2c) through Compound (3). In this case, Compound (3) is synthesized by reacting one mole of Compound (2c) with 1–2 moles of an epoxymethylating agent such as trimethylsulfoxonium iodide or trimethylsulfonium iodide in a solvent in the presence of 2–5 moles of a base. As the solvent, dimethylsulfoxide can be suitably used. It is possible to add diethyl ether, tetrahydrofuran or the like to the solvent as needed. Examples of the base include sodium hydroxide, potassium hydroxide, barium hydroxide, sodium carbonate, potassium carbonate and sodium hydride. Of these, sodium hydride is particularly preferred. The reaction temperature falls within a range of −100° C. to the boiling point of the solvent, with a range of from −40° C. to 50° C. being particularly preferred.

Step (3-1a)

The synthesis of Compound (1a) from Compound (3) is conducted by reacting Compound (3) with 1,2,4-triazole or an alkali metal salt thereof in a solvent in the presence of a base. As the solvent, N,N-dimethylformamide, acetonitrile, N,N-dimethylacetamide or dimethylsulfoxide can be used suitably. Examples of the base include sodium hydroxide, potassium hydroxide, barium hydroxide, sodium carbonate, potassium carbonate and tert-butoxypotassium. The reaction temperature falls within a range of from 0° C. to the boiling point of the solvent, with 20° C. to 60° C. being particularly preferred.

Step (1a-1b)

Compound (1b) can be prepared by reacting one mole of Compound (1a) with about one equivalent, preferably about 1.2 equivalents of an oxidizing agent. Examples of the oxidizing agent include m-chloroperbenzoic acid, hydrogen peroxide, peracetic acid, tetrapropylammonium perruthenate, osmium tetraoxide, potassium permanganate and oxone. Illustrative of the usable solvent include chloroform, dichloromethane, acetic acid, methanol, water and acetonitrile. The reaction temperature ranges from –40° C. to the boiling point of the solvent, with a range of from 0° C. to 50° C. being preferred. To improve the yield, a catalyst can be used. Examples of such a catalyst include selenium dioxide, sodium tungstate, sodium molybdate and vanadium oxide, with sodium tungstate being preferred.

Step (1b-1c) and Step (1a-1c)

Compound (1c) can be prepared by reacting one mole of Compound (1b) obtained above with 1.0–2.0 equivalents, preferably about 1.2 equivalents of an oxidizing agent. Compound (1c) can also be prepared by reacting one mole of Compound (1a) with at least 2 equivalents, preferably 2.2–2.5 equivalents of an oxidizing agent. The oxidizing agent, solvent, catalyst and reaction temperature to be employed are similar to those described in the above step (1a-1b).

Since in the compounds (1a) and (1c), a carbon atom to which a hydroxyl group is bonded is an asymmetric center, each compound has two enantiomers. Compound (1b) on the other hand has two diastereomers based on two asymmetric centers of the carbon atom and sulfoxide. They can be separated by the following method.

Compound (1a) has two enantiomers based on an asymmetric carbon atom. The optically active substance can be prepared by separating the compound by using a column for the separation of optical isomer. Examples of the optically active stationary phase include optically active synthetic polymers, natural macromolecules and metal complexes of an amino acid, with silica gel coated with a cellulose derivative being preferred. As a column filled with the silica gel coated with a cellulose derivative, a commercially-available column such as "Chiral Cell OD" and "Chiral Pack AS" (trade names; products of Daicel Chemical Industries) can be employed, with "Chiral Cell OD" being particularly preferred. As the type of chromatography, liquid chromatography is preferred. In this case, usable examples of an eluent as a mobile phase include hexane-ethanol and hexane-isopropyl alcohol. Alternatively, an optical active substance can be prepared by optical resolution. Illustrative of a reagent for optical resolution include optically active camphor-sulfonic acid which may be substituted by a halogen atom, and salts thereof. Specific examples include (+)-camphor-10-sulfonic acid, (−)-camphor-10-sulfonic acid, (+)-3-bromocamphor-8-sulfonic acid, (−)-3-bromocamphor-8-sulfonic acid, (+)-3-bromocamphor-10-sulfonic acid, (−)-3-bromocamphor-10-sulfonic acid, ammonium (+)-3-bromocamphor-8-sulfonate and ammonium (−)-3-bromocamphor-8-sulfonate. Of these, (+)-3-bromocamphor-8-sulfonic acid, (−)-3-bromocamphor-8-sulfonic acid, ammonium (+)-3-bromocamphor-8-sulfonate and ammonium (−)-3-bromocamphor-8-sulfonate are particularly preferred.

As described above, Compound (1b) has two diastereomers. The separation can be effected by subjecting the compound to chromatography on a silica gel column using, for example, a 19:1 mixed eluent of chloroform and methanol.

Compound (1c) has two enantiomers based on an asymmetric carbon. The optical active substance can be prepared by optical resolution similar to that employed for Compound (1a). Alternatively, it can be prepared by the above-described oxidizing reaction using the optical active substance of Compound (1a) or (1b).

Compound (1) of the present invention can be prepared as a pharmaceutical, particularly, a mycocide in various dosage forms such as tablets, granules, powders, capsules, suspending agents, injections, suppositories and external preparations and the like. In this case, the pharmaceutical can be prepared by incorporating a pharmacologically acceptable vehicle. Described specifically, a solid preparation can be obtained in a conventional manner by adding an excipient and optionally a binder, disintegrator, coating agent and/or the like to Compound (1) of the present invention. An injection may be prepared by dissolving, dispersing or emulsifying Compound (1) of the present invention in an aqueous carrier such as distilled water for injection or by preparing powder for injection and dissolving it upon use. Examples of the administration method include intravenous administration, intraarterial administration, subcutaneous administration and instillation.

When Compound (1) of the present invention or salt thereof is used as a pharmaceutical, the administration amount differs depending on various factors such as the kind of the disease, symptoms, weight, age, sex or administration route. When used as a mycocide, Compound (1) of the present invention or salt thereof is administered in an amount of 0.1–1000 mg/day, preferably 5–100 mg/day. This amount can be administered once a day or 2–4 times in a day.

EXAMPLES

The present invention will hereinafter be described in detail by Referential Examples and Examples. It should however be borne in mind that the present invention will not be limited to or by the following examples.

REFERENCE EXAMPLE 1

Synthesis of 2',4'-difluoro-2-(methylthio) acetophenone

[Compound (2a-1)]

To a 500 ml solution of 50 g (0.262 mol) of 2-chloro-2', 4'-difluoroacetophenone [Compound (4)-1] in methanol, 147 g (0.314 mol) of a 15% aqueous solution of sodium methylmercaptan were added dropwise under ice cooling, followed by stirring at room temperature for 2 hours. The solvent was distilled off under reduced pressure. Water was then added to the reaction mixture and they were mixed. The resulting mixture was extracted with chloroform. The extract was washed successively with water and saturated saline and then, dried over anhydrous magnesium sulfate. The solvent was thereafter distilled off under reduced pressure. The oil so obtained was distilled under reduced pressure (93–95° C., 3 mmHg), whereby 47.3 g of the title Compound (2a-1) were obtained as a colorless oil (yield: 89.2%).

$^1$H-NMR(CDCl$_3$)δ ppm: 2.10(s,3H), 3.77(d,2H), 6.80–7.18(m,2H), 7.92–8.20(m,1H)

EXAMPLE 1

Synthesis of 2-methylthio-2,2,2',4'-tetrafluoroacetophenone [Compound (2c-1)]

(1) Synthesis of Compound (2c-1) using N-fluoro-4-methylpyridinium-2-sulfonate To a 20 ml solution of 0.5 g (2.5 mmol) of 2',4'-difluoro-2-(methylthio)acetophenone [Compound (2a-1)] in 1,1,2-trichloroethane, 1.7 g (8.9 mmol) of N-fluoro-4-methylpyridinium-2-sulfonate ("MEC-02", trade name; product of Daikin Industries, Ltd.) were added at an internal temperature of 80° C., followed by stirring at an internal temperature of 100° C. for 30 minutes. After cooling, the reaction mixture was added to n-hexane. The insoluble matter so precipitated was filtered off. The insoluble matter was then washed with ether, followed by combination with the hexane layer. The layers so combined were washed successively with water and saturated saline, followed by drying over anhydrous magnesium sulfate. The solvent was then distilled off under reduced pressure. The residue so obtained was subjected to chromatography on a silica gel column using chloroform, whereby 0.30 g of the title Compound (2c-1) was obtained in the form of a light yellow oil (yield: 50.8%).

$^1$H-NMR(CDCl$_3$)δ ppm: 2.35(t,3H), 6.91–7.05(m,2H), 7.94–8.00(m,1H).

(2) Synthesis of Compound (2c-1) using N-fluoropyridinium triflate

To a 20 ml solution of 0.5 g (2.5 mmol) of 2',4'-difluoro-2-(methylthio)acetophenone [Compound (2a-1)] in 1,1,2-trichloroethane, 3.0 g (12.1 mmol) of N-fluoropyridinium triflate ("Onoda Fluorinate FP-T500", trade name; product of Chichibu Onoda Co., Ltd.) were added at an internal temperature of 80° C., followed by stirring at an internal temperature of 100° C. for one hour. After cooling, the reaction mixture was added to n-hexane. The insoluble matter precipitated was filtered off. The insoluble matter was then washed with ethyl ether, followed by combination with the hexane layer. The layers so combined were washed successively with water and saturated saline, followed by drying over anhydrous magnesium sulfate. The solvent was distilled off under reduced pressure. The residue so obtained was subjected to chromatography on a silica gel column using chloroform, whereby 0.28 g of the title Compound (2c-1) was obtained in the form of a light yellow oil (yield: 47.5%).

EXAMPLE 2

Synthesis of 2-methylthio-2,2,2',4'-tetrafluoroacetophenone [Compound (2c-1)] through 2-methylthio-2,2',4'-trifluoroacetophenone [Compound (2b-1)]

(1) Synthesis of 2-methylthio-2,2',4'-trifluoroacetophenone [Compound (2b-1)]

To a 20 ml solution of 0.5 g (2.5 mmol) of 2',4'-difluoro-2-(methylthio)acetophenone [Compound (2a-1)] in 1,2-dichloroethane, 1.1 g (3.8 mmol) of N-fluoro-2,4,6-trimethylpyridinium triflate ("Onoda Florinate FP-T300", trade name; product of Chichibu Onoda Co., Ltd.) were added at room temperature, followed by stirring at the same temperature for 12 hours. The reaction mixture was added to n-hexane. The insoluble matter so precipitated was filtered off. The insoluble matter was then washed with ethyl ether, followed by combination with the hexane layer. The layers so combined were washed successively with water and saturated saline, followed by drying over anhydrous magnesium sulfate. The solvent was then distilled off under reduced pressure, whereby 0.50 g of the title Compound (2b-1) was obtained in the form of a light yellow oil (yield: 91.7%).

$^1$H-NMR(CDCl$_3$)δ ppm: 2.10(d,3H), 6.70(d,1H), 6.80–7.20(m,2H), 7.95–8.30(m,1H).

(2) Synthesis of 2-methylthio-2,2,2',4'-tetrafluoroacetophenone [Compound (2c-1)]

In a 20 ml solution of 0.5 g (2.3 mmol) of 2-methylthio-2,2',4'-trifluoroacetophenone [Compound (2b-1)] in 1,1,2-trichloroethane, 0.7 g (3.7 mmol) of N-fluoro-4-methylpyridinium-2-sulfonate ("MEC-02", trade name; Daikin Industries, Ltd.) was added at an internal temperature of 80° C., followed by stirring at an internal temperature of 100° C. for 20 minutes. After cooling, the reaction mixture was added to n-hexane. The insoluble matter so precipitated was filtered off. The insoluble matter was then washed with ethyl ether, followed by combination with the hexane layer. The layers so combined were washed successively with water and saturated saline, followed by drying over anhydrous magnesium sulfate. The solvent was then distilled off under reduced pressure. The residue so obtained was subjected to chromatography on a silica gel column using chloroform, whereby 0.26 g of the title Compound (2c-1) was obtained in the form of a light yellow oil (yield: 48.1%).

EXAMPLE 3

Synthesis of 2-methylthio-2,2,4'-trifluoroacetophenone [Compound (2c-2)]

In a similar manner to Example 1(1) except that 1.0 g (5.4 mmol) of 4'-fluoro-2-(methylthio)acetophenone [Compound (2a-2)] was used instead of Compound (2a-1), 0.54 g of the title Compound (2c-2) was obtained in the form of a light yellow oil (yield: 45.0%).

$^1$H-NMR(CDCl$_3$)δ ppm: 2.37(t,3H), 7.15–7.22(m,2H), 8.18–8.20(m,2H).

EXAMPLE 4

Synthesis of 2',4'-dichloro-2,2-difluoro-2-(methylthio)acetophenone [Compound (2c-3)]

In a similar manner to Example 1(1) except that 2.0 g (8.5 mmol) of 2',4'-dichloro-2-(methylthio)acetophenone [Compound (2a-3)] were used instead of Compound (2a-1), 0.60 g of the title Compound (2c-3) was obtained in the form of a light yellow oil (yield: 26.0%).

$^1$H-NMR(CDCl$_3$)δ ppm: 2.35(t,3H), 7.34(dd,1H), 7.52(d, 1H), 7.68(d,1H).

EXAMPLE 5

Synthesis of 2,2-difluoro-2-methylthio-4'-(trifluoromethyl)acetophenone [Compound (2c-4)]

In a similar manner to Example 1(1) except that 2.0 g (7.7 mmol) of 2-chloro-4'-(trifluoromethyl)acetophenone [Compound (2a-4)] were used instead of Compound (2a-1), 1.0 g of the title Compound (2c-4) was obtained in the form of a light yellow oil (yield: 48.0%).

$^1$H-NMR(CDCl$_3$)δ ppm: 2.24(t,3H), 7.81(d,2H), 8.24(d, 2H).

EXAMPLE 6

Synthesis of 2,2-difluoro-2-(methylthio) acetophenone [Compound (2c-5)]

To a 50 ml solution of 3.8 g (19.9 mmol) of 2-chloro-2,2-difluoroacetophenone [Compound (5-1)] in methanol, 11.2 g (23.9 mmol) of a 15% aqueous solution of sodium methylmercaptan were added dropwise under ice cooling, followed by stirring at 35° C. for 2 hours. The solvent was distilled off under reduced pressure. To the reaction mixture, water was added, followed by extraction with chloroform. The chloroform extract was washed successively with water and saturated saline, followed by drying over anhydrous magnesium sulfate. The solvent was then distilled off, whereby 3.1 g of the title Compound (2c-5) were obtained in the form of a colorless oil (yield: 78.0%).

$^1$H-NMR(CDCl$_3$)δ ppm: 2.39(t,3H), 7.30–7.80(m,3H), 8.10–8.30(m,2H).

EXAMPLE 7

Synthesis of 2-(1,1-difluoro-1-methylthio)methyl-2-(2',4'-difluorophenyl)oxirane [Compound (3-1)]

To 10 ml of dimethylsulfoxide and 20 ml of tetrahydrofuran, 0.09 g (2.3 mmol) of 60% sodium hydride (washed with n-hexane) was added, followed by heating to 55° C.. To the resulting mixture, 0.53 g (2.4 mmol) of trimethylsulfoxonium iodide was added in portions, followed by stirring at the same temperature for 15 minutes. The reaction mixture was cooled to −10° C., to which a 10 ml solution of 0.48 g (2.0 mmol) of 2-methylthio-2,2,2',4'-tetrafluoroacetophenone [Compound (2c-1)] in tetrahydrofuran was added dropwise. The resulting mixture was allowed to rise back to room temperature and stirred for one hour. The reaction mixture was poured into ice water and extracted with ethyl ether. The extract was washed successively with water and saturated saline, followed by drying over anhydrous magnesium sulfate. The solvent was distilled off under reduced pressure, whereby 0.48 g of the title Compound (3-1) was obtained in the form of a light yellow oil (yield: 94.1%).

$^1$H-NMR(CDCl$_3$)δ ppm: 2.28(br.s,3H), 2.99(m,1H), 3.48(d,1H), 6.81–6.94(m,2H), 7.50–7.56(m,1H).

EXAMPLE 8

Synthesis of 2-(1,1-difluoro-1-methylthio)methyl-2-(4'-fluorophenyl)oxirane [Compound (3-2)]

In a similar manner to Example 7 except that 0.54 g (2.0 mmol) of 2-methylthio-2,2,4'-trifluoroacetophenone [Compound (2c-2)] was used instead of Compound (2c-1), 0.55 g of the title Compound (3-2) was obtained in the form of a light yellow oil (yield: 96.5%).

$^1$H-NMR(CDCl$_3$)δ ppm: 2.28(br.s,3H), 2.85(m,1H), 3.46(d,1H), 7.04–7.09(m,2H), 7.51–7.54(m,2H).

EXAMPLE 9

Synthesis of 2-(2',4'-dichlorophenyl)-2-(1,1-difluoro-1-methylthio)methyloxirane [Compound (3-3)]

In a similar manner to Example 7 except that 0.60 g (2.2 mmol) of 2',4'-dichloro-2,2-difluoro-2-(methylthio) acetophenone [Compound (2c-3)] instead of Compound (2c-1), 0.52 g of the title Compound (3-3) was obtained in the form of a light yellow oil (yield: 82.5%).

$^1$H-NMR(CDCl$_3$)δ ppm: 2.29(br.s,3H), 3.03(m,1H), 3.57(d,1H), 7.30(dd,1H), 7.42(d,H), 7.54(d,1H)

EXAMPLE 10

Synthesis of 2-(1,1-difluoro-1-methylthio)methyl-2-[4'-(trifluoromethyl)phenyl]oxirane [Compound (3-4)]

In a similar manner to Example 7 except that 1.0 g (3.7 mmol) of 2,2-difluoro-2-methylthio-4'-(trifluoromethyl) acetophenone [Compound (2c-4)] was used instead of Compound (2c-1), 1.05 g of the title Compound (3-4) was obtained in the form of a light yellow oil (yield: 99.9%).

$^1$H-NMR(CDCl$_3$)δ ppm: 2.29(br.s,3H), 2.85(m,1H), 3.50(d,1H), 7.66(s,4H).

EXAMPLE 11

Synthesis of 2-(1,l-difluoro-1-methylthio)methyl-2-phenyloxirane [Compound (3-5)]

In a similar manner to Example 7 except that 1.0 g (5.0 mmol) of 2,2-difluoro-2-(methylthio)acetophenone [Compound (2c-5)] was used instead of Compound (2c-1), 1.02 g of the title Compound (3-5) was obtained in the form of a light yellow oil (yield: 95.3%).

$^1$H-NMR(CDCl$_3$)δ ppm: 2.26(br.s,3H), 2.85(m,1H), 3.46(d,1H), 7.32–7.49(m,5H).

EXAMPLE 12

Synthesis of 3,3-difluoro-2-(2',4'-difluorophenyl)-3-methylthio-1-(1H-1,2,4-triazol-1-yl)propan-2-ol [Compound (1a-1)]

To a 20 ml solution of 0.48 g (1.9 mmol) of 2-(1,1-difluoro-1-methylthio)methyl-2-(2',4'-difluorophenyl) oxirane [Compound (3-1)] in N,N-dimethylformamide, 0.50 g (7.2 mmol) of 1,2,4-triazole and 1.00 g (7.2 mmol) of anhydrous potassium carbonate were added, followed by added, followed by stirring at 55° C. for 1.5 hours. The solvent was distilled off under reduced pressure. To the residue, ethyl ether was added, followed by washing successively with water and saturated saline and drying over anhydrous magnesium sulfate. The solvent was then distilled off under reduced pressure. The oil so obtained was purified by chromatography on a silica gel column using chloroform, whereby 0.44 g of the title Compound (1a-1) was obtained in the form of colorless crystals (yield: 72.1%).

Melting point: 122–123° C.

IR(KBr) ν$_{max}$cm$^{-1}$: 3136, 1618, 1499, 1145

MS(FAB): 322(M+H)$^+$ $^1$H-NMR(CDCl$_3$)δ ppm: 2.27(t,3H), 4.82(d,1H), 5.28(d,1H), 5.78(s,1H), 6.71–6.88(m,2H), 7.71–7.77(m,1H), 7.80(s,1H), 8.09(s,1H).

EXAMPLE 13

Synthesis of 3,3-difluoro-2-(4'-fluorophenyl)-3-methylthio-1-(1H-1,2,4-triazol-1-yl)propan-2-ol [Compound (1a-2)]

In a similar manner to Example 12 except that 0.55 g (2.4 mmol) of 2-(1,1-difluoro-1-methylthio)methyl-2-(4'-fluorophenyl)oxirane [Compound (3-2)] was used instead of Compound (3-1), 0.50 g of the title Compound (1a-2) was obtained in the form of colorless crystals (yield: 70.4%).

Melting point: 117–118° C.

IR(KBr)$v_{max}$cm$^{-1}$: 3137, 1607, 1510, 1133

MS(FAB): 304(M+H)$^+$ $^1$H-NMR(CDCl$_3$)δ ppm: 2.23(t,3H), 4.73(d,1H), 4.89(d, 1H), 5.31(s,1H), 7.01–7.05(m,2H), 7.52–7.55(m,2H), 7.86 (s,1H), 7.92(s,1H).

EXAMPLE 14

Synthesis of 2-(2',4'-dichlorophenyl)-3,3-difluoro-3-methylthio-1-(1H-1,2,4-triazol-1-yl)propan-2-ol [Compound (1a-3)]

In a similar manner to Example 12 except that 0.52 g (1.8 mmol) of 2-(2',4'-dichlorophenyl)-2-(1,1-difluoro-1-methylthio)methyloxirane [Compound (3-3)] was used instead of Compound (3-1), 0.45 g of the title Compound (1a-3) was obtained in the form of colorless crystals (yield: 69.2%).

Melting point: 143–146° C.

IR(KBr)$v_{max}$cm$^{-1}$: 3138, 1587, 1518, 1105

MS(FAB): 354(M+H)$^+$ $^1$H-NMR(CDCl$_3$)δ ppm: 2.27(t,3H), 4.87(d,1H), 5.82(d, 1H), 5.93(s,1H), 7.23(dd,1H), 7.32(d,1H), 7.83(s,1H), 7.90 (d,1H), 8.20(s,1H).

EXAMPLE 15

Synthesis of 3,3-difluoro-3-methylthio-1-(1H-1,2,4-triazol-1-yl)-2-[4'-(trifluoromethyl)phenyl]propan-2-ol [Compound (1a-4)]

In a similar manner to Example 12 except that 1.05 g (3.7 mmol) of 2-(1,1-difluoro-1-methylthio)methyl-2-[4'-(trifluoromethyl)phenyl]oxirane [Compound (3-4)] were used instead of Compound (3-1), 0.48 g of the title Compound (1a-4) was obtained in the form of colorless crystals (yield: 36.5%).

Melting point: 110–112° C.

IR(KBr)$v_{max}$cm$^{-1}$: 3010, 1620, 1515, 1122

MS(FAB): 354(M+H)$^+$ $^1$H-NMR(CDCl$_3$)δ ppm: 2.24(t,3H), 4.77(d,1H), 4.92(d, 1H), 5.52(s,1H), 7.61(d,2H), 7.70(d,2H), 7.86(s,1H), 7.95 (s,1H).

EXAMPLE 16

Synthesis of 3,3-difluoro-3-methylthio-2-phenyl-1-(1H-1,2,4-triazol-1-yl)propan-2-ol [Compound (1a-5)]

In a similar manner to Example 12 except that 1.02 g (4.7 mmol) of 2-(1,1-difluoro-1-methylthio)methyl-2-phenyloxirane [Compound (3-5)] instead of Compound (3-1), 0.54 g of the title Compound (1a-5) was obtained in the form of colorless crystals (yield: 38.0%).

Melting point: 130–132° C.

IR(KBr)$v_{max}$cm$^{-1}$: 3135, 1516, 1498, 1135

MS(FAB): 318(M+H)$^+$ $^1$H-NMR(CDCl$_3$)δ ppm: 3.14(t,3H), 4.89(d,1H), 5.28(d, 1H), 5.94(s,1H), 7.33–7.37(m,3H), 7.49–7.51(m,2H), 7.74 (s,1H), 7.83(s,1H).

EXAMPLE 17

Synthesis of 3,3-difluoro-2-(2',4'-difluorophenyl)-3-methylsulfonyl-1-(1H-1,2,4-triazol-1-yl)propan-2-ol [Compound (1c-1)]

To a 10 ml solution of 0.50 g (1.6 mol) of 3,3-difluoro-2-(2',4'-difluorophenyl)-3-methylthio-1-(1H-1,2,4-triazole-1-yl)-propan-2-ol [Compound (1a-1)] in methanol, 0.01 q (0.03 mmol) of sodium tungstate dihydrate was added, followed by the dropwise addition of 0.53 g (4.7 mmol) of a 30% aqueous solution of hydrogen peroxide at room temperature under stirring. The resulting mixture was stirred at room temperature for 16 hours. To the reaction mixture, a 10% aqueous solution of sodium thiosulfate was added to decompose an excess oxidizing agent. Methanol was then distilled off under reduced pressure. To the residue, chloroform was added, followed by washing successively with water and saturated saline and drying over anhydrous magnesium sulfate. The solvent was then distilled off under reduced pressure. The crystals so precipitated were recrystallized from chloroform, whereby 8.0 g of the title Compound (1c-1) were obtained in the form of colorless crystals (yield: 74%).

Melting point: 158–160° C.

IR(KBr)$v_{max}$cm$^{-1}$: 3136, 1617, 1503, 1323

MS(FAB): 354(M+H)$^+$ $^1$H-NMR(CDCl$_3$)δ ppm: 3.22(t,3H), 5.17(d,1H), 5.34(d, 1H), 6.11(s,1H), 6.74–6.89(m,2H), 7.65–7.71(m,1H), 7.79 (s,1H), 8.06(d,1H).

EXAMPLE 18

Synthesis of 3,3-difluoro-2-(4'-fluorophenyl)-3-methylsulfonyl-1-(1H-1,2,4-triazol-1-yl)propan-2-ol [Compound (1c-2)]

In a similar manner to Example 17 except that 0.35 g (1.2 mmol) of 3,3-difluoro-2-(4'-fluoropheyl)-3-methylthio-1-(1H-1,2,4-triazol-1-yl)propan-2-ol [Compound (1a-2)] was used instead of Compound (1a-1), 0.13 g of the title Compound (1c-2) was obtained in the form of colorless crystals (yield: 33.3%).

Melting point: 169–171° C.

IR(KBr)$v_{max}$cm$^{-1}$: 3135, 1605, 1514, 1324

MS(FAB): 336(M+H)$^+$ $^1$H-NMR(CDCl$_3$)δ ppm: 3.17(t,3H), 4.84(d,1H), 5.27(d, 1H), 5.90(s,1H), 7.02–7.06(m,2H), 7.46–7.49(m,2H), 7.83 (s,1H), 7.88(s,1H).

EXAMPLE 19

Synthesis of 2-(2',4'-dichlorophenyl)-3,3-difluoro-3-methylsulfonyl-1-(1H-1,2,4-triazol-1-yl)propan-2-ol [Compound (1c-3)]

In a similar manner to Example 17 except that 0.40 g (1.1 mmol) of 2-(2',4'-dichlorophenyl)-3,3-difluoro-3-methylthio-1-(1H-1,2,4-triazol-1-yl)propan-2-ol [Compound (1a-3)] was used instead of Compound (1a-1), 0.40 g of the title Compound (1c-3) was obtained in the form of colorless crystals (yield: 91.0%).

Melting point: 147–148° C.

IR(KBr)$v_{max}$cm$^{-1}$: 3040, 1588, 1514, 1337

MS(FAB): 386(M+H)$^+$ $^1$H-NMR(CDCl$_3$)δ ppm: 3.23(t,3H), 5.21(d,1H), 5.97(d, 1H), 6.38(s,1H), 7.23(dd,1H), 7.35(d,1H), 7.81(s,1H), 7.83 (d,1H), 8.12(s,1H).

EXAMPLE 20

Synthesis of 3,3-difluoro-3-methylsulfonyl-1-(1H-1,2,4-triazol-1-yl)-2-[4'-(trifluoromethyl)phenyl] propan-2-ol [Compound (1c-4)]

In a similar manner to Example 17 except that 0.20 g (5.7 mmol) of 3,3-difluoro-3-methylthio-1-(1H-1,2,4-triazol-1- yl)-2-[4'-(trifluoromethyl)phenyl]propan-2-ol [Compound (1a-4)] was used instead of Compound (1a-1), 0.12 g of the title Compound (1c-4) was obtained in the form of colorless crystals (yield: 53.2%).

Melting point: 185–187° C.

IR(KBr)$v_{max}$cm$^{-1}$: 3029, 1619, 1521, 1326

MS(FAB): 386(M+H)$^+$ $^1$H-NMR(CDCl$_3$)δ ppm: 3.21(t,3H), 4.90(d,1H), 5.33(d, 1H), 6.13(s,1H), 7.61(d,2H), 7.65(d,2H), 7.83(s,1H), 7.89 (s,1H).

EXAMPLE 21

Synthesis of 3,3-difluoro-3-methylsulfonyl-2-phenyl-1-(1H-1,2,4-triazol-1-yl)propan-2-ol [Compound (1c-5)]

In a similar manner to Example 17 except that 0.17 g (0.6 mmol) of 3,3-difluoro-3-methylthio-2-phenyl-1-(1H-1,2,4-triazol-1-yl)propan-2-ol [Compound (1a-5)] was used instead of Compound (1a-1), 0.08 g of the title Compound (1c-5) was obtained in the form of colorless crystals (yield: 46%).

Melting point: 85–86° C.

IR(KBr)$v_{max}$cm$^{-1}$: 3023, 1617, 1510, 1320

MS(FAB): 318(M+H)$^+$ $^1$H-NMR(CDCl$_3$)δ ppm: 3.14(t,3H), 4.89(d,1H), 5.28(d, 1H), 5.94(s,1H), 7.33–7.37(m,3H), 7.49–7.51(m,2H), 7.74 (s,1H), 7.83(s,1H).

EXAMPLE 22

Synthesis of 3,3-difluoro-2-(2',4'-difluorophenyl)-3-methylsulfinyl-1-(1H-1,2,4-triazol-1-yl)propan-2-ol [Compound (1b-1)]

To a 10 ml solution of 150 mg (0.47 mmol) of 3,3-difluoro-2-(2',4'-difluorophenyl)-3-methylthio-1-(1H-1,2,4-triazol-1-yl)propan-2-ol [Compound (1a-1)] in methylene chloride, 114 mg (0.56 mmol) of m-chloroperbenzoic acid were added at room temperature, followed by stirring for 30 minutes. To the reaction mixture, water was added, followed by extraction with chloroform. The extract was then washed successively with a 10% aqueous solution of sodium thiosulfate and a 10% aqueous solution of sodium carbonate, followed by drying over anhydrous magnesium sulfate. The solvent was distilled off under reduced pressure. The oil so obtained was purified by chromatography on a silica gel column using chloroform : methanol (10:1), whereby 64 mg of the title Compound (1b-1) [diastereomers (1b-1A):(1b-1B)=2.5:1] were obtained in the form of colorless crystals (yield: 40%).

EXAMPLE 23

Separation of the diastereomers (1b-1A) and (1b-1B)

1.1 g of 3,3-difluoro-2-(2',4'-difluorophenyl)-3-methylsulfinyl-1-(1H-1,2,4-triazol-1-yl)propan-2-ol [Compound (1b-1)] were subjected to a moderate-pressure silica gel chromatography [column: "ULTRA PACK SI-40B", trade name; product of Yamazen Co., Ltd., 26×300 mm, a flow rate: 8 ml/min, wavelength: 254 nm] using chloroform methanol (19:1), whereby 418 mg (yield: 38%) of the diastereomer (1b-1A) and 242 mg (yield: 22%) of the diastereomer (1b-1B) were obtained in the form of colorless crystals.

(1) Diastereomer [Compound (1b-1A)]

Melting point: 154–155° C.

IR(KBr)$v_{max}$cm$^{-1}$: 3150, 1617, 1505

MS(FAB): 338(M+H)$^+$ $^1$H-NMR(CDCl$_3$)δ ppm: 2.71(t,3H), 5.09(d,1H), 5.31(d, 1H), 6.12(s,1H), 6.78–6.89(m,2H), 7.60–7.66(m,1H), 7.76 (s,1H), 8.12(s,1H).

(2) Diastereomer [Compound (1b-1B)]

Melting point: 152–153° C.

IR(KBr)$v_{max}$cm$^{-1}$: 1618, 1505, 1113

MS(FAB): 338(M+H)$^+$ $^1$H-NMR(CDCl$_3$)δ ppm: 2.78(t,3H), 4.92(d,1H), 5.31(d, 1H), 6.07(s,1H), 6.80–6.89(m,2H), 7.60–7.67(m,1H), 7.84 (s,1H), 8.16(s,1H).

EXAMPLE 24

Separation of 3,3-difluoro-2-(2',4'-difluorophenyl)-3-methylthio-1-(1H-1,2,4-triazol-1-yl)propan-2-ol [Compound (1a-1)] into (+) and (−) isomers 50 mg of a racemic modification of 3,3-difluoro-2-(2',4'-difluoropheyl)-3-methylthio-1-(1H-1,2,4-triazol-1-yl) propan-2-ol [Compound (1a-1)] were subjected to chiral separation column chromatography ["Chiral Cell OD", trade name; product of Daicell Chemical Industries Co., Ltd.). The separation into each enantiomer was conducted using hexane:isopropyl alcohol (19:1) as a mobile phase. From the fraction eluted first, 20 mg of the (−) isomer (yield: 40.0%, optical purity: 99.4%e.e.) were obtained in the form of colorless crystals, while from the fraction eluted subsequently, 21 mg of the (+) isomer (yield: 42.0%, optical purity: 99.2%e.e.) were obtained in the form of colorless crystals.

(1) (−)-3,3-difluoro-2-(2',4'-difluorophenyl)-3-methylthio-1-(1H-1,2,4-triazol-1-yl)propan-2-ol [(−)-Compound (1a-1)]

$[α]^{25}_D$ −65.0° (C=0.5, acetone)

Melting point: 154–156° C.

IR(KBr)$v_{max}$cm$^{-1}$: 3136, 1618, 1499, 1145

MS(FAB): 322(M+H)$^+$ $^1$H-NMR(CDCl$_3$)δ ppm: 2.27(t,3H), 4.82(d,1H), 5.28(d, 1H), 5.78(s,1H), 6.71–6.88(m,2H), 7.71–7.77(m,1H), 7.80 (s,1H), 8.09(d,1H).

(2) (+)-3,3-difluoro-2-(2',4'-difluorophenyl)-3-methylthio-1-(1H-1,2,4-triazol-1-yl)propan-2-ol [((+)-Compound (1a-1)]

$[α]^{25}_D$+64.6° (C=0.5, acetone)

Melting point: 154–156° C.

IR(KBr)$v_{max}$cm$^{-1}$: 3136, 1618, 1499, 1145

MS(FAB): 322(M+H)$^+$ $^1$H-NMR(CDCl$_3$)δ ppm: 2.27(t,3H), 4.82(d,1H), 5.28(d, 1H), 5.78(s,1H), 6.71–6.88(m,2H), 7.71–7.77(m,1H), 7.80 (s,1H), 8.09(d,1H).

EXAMPLE 25

Separation of 2-(2',4'-dichlorphenyl)-3,3-difluoro-3-methylthio-1-(1H-1,2,4-triazol-1-yl)propan-2-ol [Compound (1a-3)] into (+) and (−) isomers In accordance with a manner similar to Example 24, from 100 mg of a racemic modification of 2-(2',4'- dichlorophenyl)-3,3-difluoro-3-methylthio-1-(1H-1,2,4-triazol-1-yl)propan-2-ol [Compound (1a-3)], 48 mg of the (−) isomer in the form of colorless crystals (yield: 48.0%, optical purity: 99.1%e.e.) and 41 mg of the (+) isomer (yield: 41.0%, optical purity: 99.3%e.e.) in the form of colorless crystals were obtained in this order of elution.

(1) (−)-2-(2',4'-dichlorophenyl)-3,3-difluoro-3-methylthio-1-(1H-1,2,4-triazol-1-yl)propan-2-ol [(−)-Compound (1a-3)]

$[\alpha]^{25}_D$ −87.5° (C=0.02, methanol)
Melting point: 120–123° C.
IR(KBr)$\nu_{max}$cm$^{-1}$: 3138, 1587, 1518, 1105
MS (FAB): 354 (M+H)$^+$
$^1$H-NMR(CDCl$_3$)δ ppm: 2.27(t,3H), 4.87(d,1H), 5.82(d,1H), 5.93(s,1H), 7.23(dd,1H), 7.32(d,1H), 7.83(s,1H), 7.90 (s,1H), 8.20(s,1H).

(2) (+)-2-(2',4'-dichlorophenyl)-3,3-difluoro-3-methylthio- 1-(1H-1,2,4-triazol-1-yl)propan-2-ol [(+)-Compound (1a-3)]

$[\alpha]^{25}_D$ +85.0° (C=0.03, methanol)
Melting point: 121–123° C.
IR(KBr)$\nu_{max}$cm$^{-1}$: 3138, 1587, 1518, 1105
MS(FAB): 354(M+H)$^+$
$^1$H-NMR(CDCl$_3$)δ ppm: 2.27(t,3H), 4.87(d,1H), 5.82(d,1H), 5.93(s,1H), 7.23(dd,1H), 7.32(d,1H), 7.83(s,1H), 7.90 (d,1H), 8.20(s,1H).

EXAMPLE 26

Synthesis of (−)-3,3-difluoro-2-(2',4'-difluorophenyl)-3-methylsulfonyl-1-(1H-1,2,4-triazol-1-yl)propan-2-ol Compound (1c-1)] by the oxidation of (−)-3,3-difluoro-2-(2',4'-difluorophenyl)-3-methylthio-1-(1H-1,2,4-triazol-1-yl)propan-2-ol [(−)-Compound (1a-1]

In accordance with a manner similar to Example 17, from 59 mg of the (−)-Compound (1a-1), 54 mg of the (−)-Compound (1c-1) (yield: 83.2%, optical purity: 99.7%e.e.) were obtained in the form of colorless crystals.

$[\alpha]^{25}_D$ −28.0° (C=0.25, acetone)
Melting point: 102–103° C.
IR(KBr)$\nu_{max}$cm$^{-1}$: 3136, 1617, 1503, 1323
MS(FAB): 354(M+H)$^+$
$^1$H-NMR(CDCl$_3$)δ ppm: 3.22(t,3H), 5.17(d,1H), 5.34(d,1H), 6.11(s,1H), 6.74–6.89(m,2H), 7.65–7.71(m,1H), 7.79 (s,1H), 8.06(d,1H).

EXAMPLE 27

Synthesis of (+)-3,3-difluoro-2-(2',4'-difluorophenyl)-3-methylsulfonyl-1-(1H-1,2,4-triazol-1-yl)propan-2-ol [(+)-Compound (1c-1)] by the oxidation of (+)-3,3-difluoro-2-(2',4'-difluorophenyl)-3-methylthio-1-(1H-1,2,4-triazol-1-yl)propan-2-ol [(+)-Compound (1a-1]

In accordance with a manner similar to Example 17, from 100 mg of the (+)-Compound (1a-1), 107 mg of the (+)-Compound (1c-1) (yield: 97.3%, optical purity: 99.5%e.e.) were obtained in the form of colorless crystals.

$[\alpha]^{25}_D$ +28.4° (C=0.125, acetone)
Melting point: 102–103° C.+

IR(KBr)$\nu_{max}$cm$^{-1}$: 3136, 1617, 1503, 1323
MS(FAB): 354(M+H)$^+$
$^1$H-NMR(CDCl$_3$)δ ppm: 3.22(t,3H), 5.17(d,1H), 5.34(d,1H), 6.11(s,1H), 6.74–6.89(m,2H), 7.65–7.71(m,1H), 7.79 (s,1H), 8.06(d,1H).

EXAMPLE 28

Synthesis of (−)-2-(2',4'-dichlorophenyl)-3,3-difluoro-3-methylsulfonyl-1-(1H-1,2,4-triazol-1-yl) propan-2-ol [(−)-Compound (1c-3)]

In accordance with a manner similar to Example 17, from 48 mg of (−)-2-(2',4'-dichlorophenyl)-3,3-difluoro-3-methylthio-1-(1H-1,2,4-triazol-1-yl)propan-2-ol [(−)-Compound (1a-3), 38 mg of the title Compound (−)-(1c-3) (yield: 72.7%, optical purity: 96.9%e.e.) were obtained in the form of colorless crystals.

$[\alpha]^{20}_D$ −29.5° (C=0.1, methanol)
Melting point: 165–167° C.
IR(KBr)$\nu_{max}$cm$^{-1}$: 3040, 1588, 1514, 1337
MS(FAB): 386(M+H)$^+$
$^1$H-NMR(CDCl$_3$)δ ppm: 3.23(t,3H), 5.21(d,1H), 5.97(d,1H), 6.38(s,1H), 7.23(dd,1H), 7.35(d,1H), 7.81(s,1H), 7.83 (d,1H), 8.12(s,1H).

EXAMPLE 29

Synthesis of (+)-2-(2',4'-dichlorophenyl)-3,3-difluoro-3-methylsulfonyl-1-(1H-1,2,4-triazol-1-yl) propan-2-ol ((+)-Compound (1c-3)]

In accordance with a manner similar to Example 17, from 41 mg of (+)-2-(2',4'-dichlorophenyl)-3,3-difluoro-3-methylthio-1-(1H-1,2,4-triazol-1-yl)propan-2-ol [(+)-Compound (1a-3), 33 mg of the title Compound (+)-(1c-3) (yield: 73.8%, optical purity: 100%e.e.) were obtained in the form of colorless crystals.

$[\alpha]^{20}_D$ +30.2° (C=0.04, methanol)
Melting point: 165–167° C.
IR(KBr)$\nu_{max}$cm$^{-1}$: 3040, 1588, 1514, 1337
MS(FAB): 386(M+H)$^+$
$^1$H-NMR(CDCl$_3$)δ ppm: 3.23(t,3H), 5.21(d,1H), 5.97(d,1H), 6.38(s,1H), 7.23(dd,1H), 7.35(d,1H), 7.81(s,1H), 7.83 (d,1H), 8.12(s,1H).

EXAMPLE 30

Separation of 3,3-difluoro-2-(4'-fluorophenyl)-3-methylsulfonyl-1-(1H-1,2,4-triazol-1-yl)propan-2-ol [Compound (1c-2)] into (+) and (−) isomers 50 mg of a racemic modification of 3,3-difluoro-2-(4'-fluorophenyl)-3-methylsulfonyl-1-(1H-1,2,4-triazol-1-yl) propan-2-ol [Compound (1c-2)] were subjected to chiral separation column chromatography ("Chiral Cell OD", trade name; Product of Daicell Chemical Industries, Ltd.) using hexane : isopropyl alcohol (3:1) as a mobile phase, whereby from the fraction eluted first, 23 mg of the (+) isomer (yield: 46.0%, optical purity: 99.8%e.e.) were obtained in the form of colorless crystals and from the fraction eluted next, 20 mg of the (−) isomer (yield: 40.0%, optical purity: 99.0%e.e.) were obtained in the form of colorless crystals.

(1) (+)-3,3-difluoro-2-(4'-fluorophenyl)-3-methylsulfonyl-1-(1H-1,2,4-triazol-1-yl)propan-2-ol [(+)-Compound (1c-2)]

$[\alpha]^{20}_D$ +27.0° (C=0.1, methanol)
Melting point: 103–106° C.

IR(KBr)ν$_{max}$cm$^{-1}$: 3135, 1605, 1514, 1324
MS(FAB): 336(M+H)$^+$
$^1$H-NMR(CDCl$_3$)δ ppm: 3.17(t,3H), 4.84(d,1H), 5.27(d, 1H), 5.90(s,1H), 7.02–7.06(m,2H), 7.46–7.49(m,2H), 7.83 (s,1H), 7.88(s,1H).

(2) (−)-3,3-difluoro-2-(4'-fluorophenyl)-3-methylsulfonyl-1-(1H-1,2,4-triazol-1-yl)propan-2-ol [(−)-Compound (1c-2)]

[α]$^{20}_D$ −31.0° (C=0.1, methanol)
Melting point: 102–105° C.
IR(KBr)ν$_{max}$cm$^{-1}$: 3135, 1605, 1514, 1324
MS(FAB): 336(M+H)$^+$
$^1$H-NMR(CDCl$_3$)δ ppm: 3.17(t,3H), 4.84(d,1H), 5.27(d, 1H), 5.90(s,1H), 7.02–7.06(m,2H), 7.46–7.49(m,2H), 7.83 (s,1H), 7.88(s,1H).

EXAMPLE 31

Separation of 3,3-difluoro-3-methylsulfonyl-1-(1H-1,2,4-triazol-1-yl)-2-[4'-(trifluoromethyl)phenyl]propan-2-ol [Compound (1c-4)] into (+) and (−) isomers In accordance with a manner similar to Example 30, from 50 mg of a racemic modification of 3,3-difluoro-3-methylsulfonyl-1-(1H-1,2,4-triazol-1-yl)-2-[4'-(trifluoromethyl)phenyl]propan-2-ol [Compound (1c-4)], 18 mg of the (+) isomer (yield: 36.0%, optical purity: 99.5%e.e.) in the form of colorless crystals and 25 mg of the (−) isomer (yield: 50.0%, optical purity: 99.4%e.e.) in the form of colorless crystals were obtained in this order of elution.

(1) (+)-3,3-difluoro-3-methylsulfonyl-1-(1H-1,2,4-triazol-1-yl)-2-[4'-(trifluoromethyl)phenyl]propan-2-ol [(+)-Compound (1c-4)]

[α]$^{20}_D$ +20.5° (C=0.1, methanol)
Melting point: 147–150° C.
IR(KBr)ν$_{max}$cm$^{-1}$: 3029, 1619, 1521, 1326
MS(FAB): 386(M+H)$^+$
$^1$H-NMR(CDCl$_3$)δ ppm: 3.21(t,3H), 4.90(d,1H), 5.33(d, 1H), 6.13(s,1H), 7.61(d,2H), 7.65(d,2H), 7.83(s,1H), 7.89 (s,1H).

(2) (−)-3,3-difluoro-3-methylsulfonyl-1-(1H-1,2,4-triazol-1-yl)-2-[4'-(trifluoromethyl)phenyl]propan-2-ol [(−)-Compound (1c-4)]

[α]$^{20}_D$ −20.0° (C=0.1, methanol)
Melting point: 153–154° C.
IR(KBr)ν$_{max}$cm$^{-1}$: 3029, 1619, 1521, 1326
MS(FAB): 386(M+H)$^+$
$^1$H-NMR(CDCl$_3$)δ ppm: 3.21(t,3H), 4.90(d,1H), 5.33(d, 1H), 6.13(s,1H), 7.61(d,2H), 7.65(d,2H), 7.83(s,1H), 7.89 (s,1H).

EXAMPLE 32

Preparation of (−)-3,3-difluoro-2-(2',4'-difluorophenyl)-3-methylsulfonyl-1-(1H-1,2,4-triazol-1-yl)propan-2-ol [(−)-Compound (1c-1)] by using a reagent for optical resolution To a 20 ml solution of 1.0 g (2.83 mmol) of (±)-Compound (1c-1) in isopropyl alcohol, a 10 ml solution of 925 mg (2.97 mmol) of (+)-3-bromocamphor-8-sulfonic acid in isopropyl alcohol was added at 70° C., followed by stirring at 90° C. for 30 minutes. After the reaction mixture was allowed to cool down to 50° C., seed crystals were inoculated, which was allowed to stand at 25° C. for 3 days. The crystals so precipitated were collected by filtration, followed by washing with isopropyl ether and drying, whereby 940 mg of the (+)-3-bromocamphor-8-sulfonate of (−)-Compound (1c-1) (yield: 50.0%, optical purity: 64.0%e.e.) were obtained in the form of colorless crystals. The salt of (−)-Compound (1c-1) was recrystallized from isopropyl alcohol in repetition, whereby 216 mg of the (+)-3-bromocaphor-8-sulfonate of the (−)-Compound (1c-1) (yield: 11.5%, optical purity: 98%e.e.) were obtained in the form of colorless crystals. To the salt so obtained, a 10% aqueous solution of potassium carbonate was added to obtain an alkaline solution, followed by extraction with ethyl acetate. The extract was washed successively with water and saturated saline, followed by drying over anhydrous magnesium sulfate. The solvent was then distilled off under reduced pressure. The oil so obtained was recrystallized from isopropyl ether, whereby 66 mg of the (−)-Compound (1c-1) (yield: 6.6%, optical purity: 98%e.e.) were obtained in the form of colorless crystals.

[α]$^{20}_D$ −28.0° (C=0.25, acetone)
Melting point: 102–103° C..

EXAMPLE 33

In vitro antifungal activity against Candida albicans

To a 10% fatal serum added Eagle's MEM medium (containing glutamine and carbonate), each of the pharmacuticals in respective concentrations and 2.0×10$^4$ cells/ml of C. albicans ATCC 44859 were added so that the final volume of each well in a 96-well microplate would be 150 μl. Incubation was then conducted at 37° C. for 20 hours using a CO$_2$ gas incubator. After incubation, a difference in the form of C. albicans was observed under an inverted microscope between the pharmaceutical-free case and pharmaceutical-added case. By comparing with the pharmaceutical-free control in which C. albicans became a hyphoid type and hyphae showed a marked growth, the minimum inhibitory concentration (ng/ml) of the pharmaceutical at which C. albicans was controlled to a yeast-type was determined. The results are shown in Table 1.

TABLE 1

| Comp'd No. | Y$^1$ | Y$^2$ | n | Minimum inhibitory concentration (μg/ml) |
|---|---|---|---|---|
| Fluconazole | — | — | — | 250 |
| Compound(1c-1) | F | F | 2 | 62.5 |
| (−)-Compound(1c-1) | F | F | 2 | 31.3 |
| (+)-Compound(1c-1) | F | F | 2 | >1000 |
| Compound(1b-1A) | F | F | 1 | 62.5 |
| Compound(1b-1B) | F | F | 1 | 500 |
| Compound(1a-1) | F | F | 0 | 7.8 |
| Compound(1c-2) | F | H | 2 | 250 |
| (+)-Compound(1c-2) | F | H | 2 | >1000 |
| (−)-Compound(1c-2) | F | H | 2 | 62.5 |
| Compound(1a-2) | F | H | 0 | 62.5 |
| Compound(1c-3) | Cl | Cl | 2 | 31.3 |
| (−)-Compound(1c-3) | Cl | Cl | 2 | 7.8 |
| (+)-Compound(1c-3) | Cl | Cl | 2 | >1000 |
| Compound(1a-3) | Cl | Cl | 0 | 3.9 |
| Compound(1c-4) | CF$_3$ | H | 2 | 125 |
| (+)-Compound(1c-4) | CF$_3$ | H | 2 | >1000 |

TABLE 1-continued

| Comp'd No. | $Y^1$ | $Y^2$ | n | Minimum inhibitory concentration ($\mu$g/ml) |
|---|---|---|---|---|
| (−)-Compound(1c-4) | $CF_3$ | H | 2 | 62.5 |
| Compound(1a-4) | $CF_3$ | H | 0 | 15.6 |
| Compound(1c-5) | H | H | 2 | 500 |
| Compound(1a-5) | H | H | 0 | 125 |

EXAMPLE 34

In vitro antifungal activity against *Aspergillus fumigatus*

0.165 M of 3-(N-morpholino)propanesulfonic acid was added as a buffer, and each of the pharmaceuticals in respective concentrations and $3.0 \times 10^4$ cells/ml of *A. fumigatus* IFM 40808 were added to RPMI MEDIUM 1640 (containing glutamine and phenol red but not containing a carbonate) which had been adjusted to pH 7 so that the final volume of each well in a 96-well microplate would be 200 $\mu$l. Incubation was then conducted at 35° C. for 24 hours. After incubation, the minimum inhibitory concentration ($\mu$g/ml) at which the growth of about 75% of hyphae was inhibited was determined by comparing the chemical-free control. Results are shown in Table 2.

TABLE 2

| Comp'd No. | $Y^1$ | $Y^2$ | n | Minimum inhibitory concentration ($\mu$g/ml) |
|---|---|---|---|---|
| Fluconazole | — | — | — | >64 |
| Compound(1c-1) | F | F | 2 | 32 |
| (−)-Compound(1c-1) | F | F | 2 | 16 |
| (+)-Compound(1c-1) | F | F | 2 | >64 |
| Compound(1b-1A) | F | F | 1 | 64 |
| Compound(1b-1B) | F | F | 1 | >64 |
| Compound(1a-1) | F | F | 0 | 4 |
| Compound(1c-2) | F | H | 2 | >64 |
| (+)-Compound(1c-2) | F | H | 2 | >64 |
| (−)-Compound(1c-2) | F | H | 2 | 64 |
| Compound(1a-2) | F | H | 0 | 16 |
| Compound(1c-3) | Cl | Cl | 2 | 32 |
| (−)-Compound(1c-3) | Cl | Cl | 2 | 32 |
| (+)-Compound(1c-3) | Cl | Cl | 2 | >64 |
| Compound(1a-3) | Cl | Cl | 0 | 2 |
| Compound(1c-4) | $CF_3$ | H | 2 | >64 |
| (+)-Compound(1c-4) | $CF_3$ | H | 2 | >64 |
| (−)-Compound(1c-4) | $CF_3$ | H | 2 | >64 |
| Compound(1a-4) | $CF_3$ | H | 0 | 16 |
| Compound(1c-5) | H | H | 2 | >64 |
| Compound(1a-5) | H | H | 0 | 16 |

EXAMPLE 35

Tablets

| (−)-Compound (1c-1) | 50 mg |
|---|---|
| Crystalline cellulose | 60 mg |
| Lactose | 33 mg |
| Hydroxypropyl cellulose | 5 mg |
| Magnesium stearate | 2 mg |
| Total | 170 mg |

The tablets having the above composition were prepared in a conventional manner. The tablets can be prepared as sugar coated tablets or film coated tablets as needed.

EXAMPLE 36

Capsules

| (−)-Compound (1c-1) | 50 mg |
|---|---|
| Light silicic anhydride | 2 mg |
| Lactose | 150 mg |
| Starch | 46 mg |
| Talc | 2 mg |
| Total | 250 mg |

The above ingredients were filled in No. 1 capsules, whereby capsules were obtained.

EXAMPLE 37

Granules

| (−)-Compound (1c-1) | 50 mg |
|---|---|
| Lactose | 600 mg |
| Corn starch | 270 mg |
| Carboxymethyl cellulose sodium | 50 mg |
| Hydroxypropyl cellulose | 30 mg |
| Total | 1000 mg |

The granules having the above composition were prepared in a conventional manner.

EXAMPLE 38

Powders

| (−)-Compound (1c-1) | 50 mg |
|---|---|
| Light silicic anhydride | 5 mg |
| Lactose | 250 mg |
| Starch | 95 mg |
| Total | 400 mg |

The powders having the above composition were prepared in a conventional manner.

EXAMPLE 39

Injection

| (−)-Compound (1c-1) | 5 mg |
|---|---|
| Hydrogenated castor oil | 85 mg |
| Propylene glycol | 10 mg |
| Glucose | 25 mg |
| Distilled water for injection | q.s. |
| Total | 1 ml n total |

The injection having the above composition was prepared in a conventional manner.

EXAMPLE 40

Intravenous Drip Infusion

| (−)-Compound (1c-1) | 50 mg |
|---|---|
| Glucose | 5000 mg |

-continued

| | |
|---|---|
| Anhydrous disodium hydrogen phosphate | 10 mg |
| Citric acid | 14.5 mg |
| Distilled water for injection | q.s. |
| Total | 100 ml in total |

The intravenous drip infusion having the above composition was prepared in a conventional manner.

What is claimed is:

1. A 2-(methylthio)acetophenone derivative represented by the following formula (2):

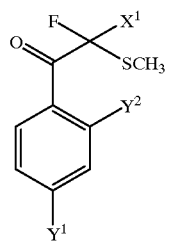

(2)

wherein $X^1$ represents a hydrogen or fluorine atom, $Y^1$ and $Y^2$ are the same or different and each independently represents a hydrogen atom, a halogen atom or a trifluoromethyl group.

* * * * *